United States Patent [19]

Terauchi et al.

[11] Patent Number: 4,820,291
[45] Date of Patent: Apr. 11, 1989

[54] URINARY APPLICANCE

[75] Inventors: Ryugo Terauchi, Tokyo; Kyoshi Fukushima, Saitama, both of Japan

[73] Assignee: Nippon Medical Supply Corporation, Tokyo, Japan

[21] Appl. No.: 75,607

[22] Filed: Jul. 20, 1987

Related U.S. Application Data

[63] Continuation of Ser. No. 835,240, Feb. 27, 1986, abandoned, which is a continuation of Ser. No. 509,431, Jun. 6, 1983, abandoned.

[51] Int. Cl.$^4$ .......................... A61F 5/44; A47K 11/00
[52] U.S. Cl. .................................... 604/349; 4/144.3; 604/73
[58] Field of Search ................ 4/144.3; 604/327, 329, 604/349–353, 368; 128/760, 761

[56] References Cited

FOREIGN PATENT DOCUMENTS 2016929  9/1979  United Kingdom ................ 604/353
8000535  4/1980  World Int. Prop. O. .......... 604/349

Primary Examiner—Charles E. Phillips
Attorney, Agent, or Firm—Bernard L. Kleinke

[57] ABSTRACT

This invention relates to a urinary appliance for use by incontinent patients. The urinary appliance of the present invention is equipped with a genital receiving bag 3 made of a soft and flexible fabric that is permeable to air, and water repellent. A urinal 8 or a urine storage bag 32 is connected to the genital receiving bag 3. A highly water-absorbent resin 34 is placed inside the urine storage bag 32 so as to absorb and gel the urine.

3 Claims, 3 Drawing Sheets

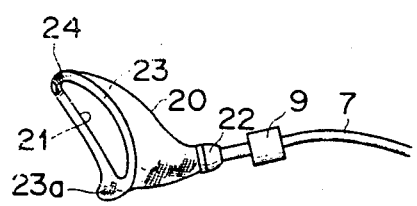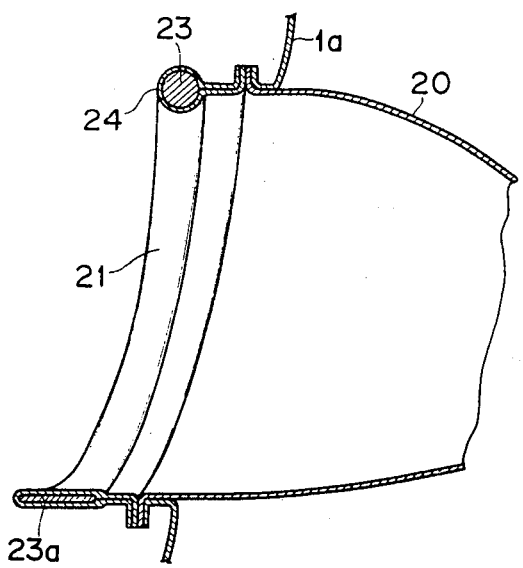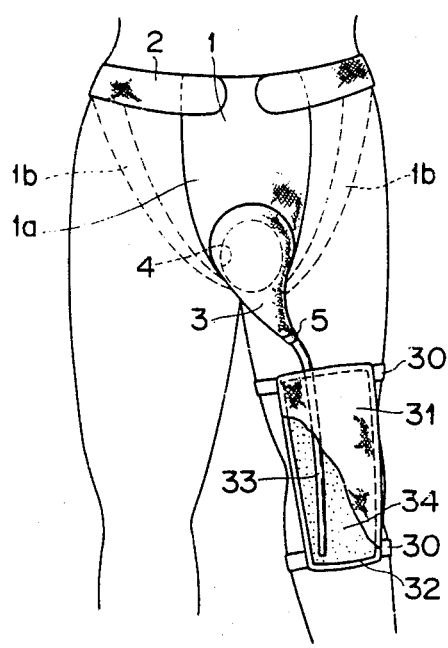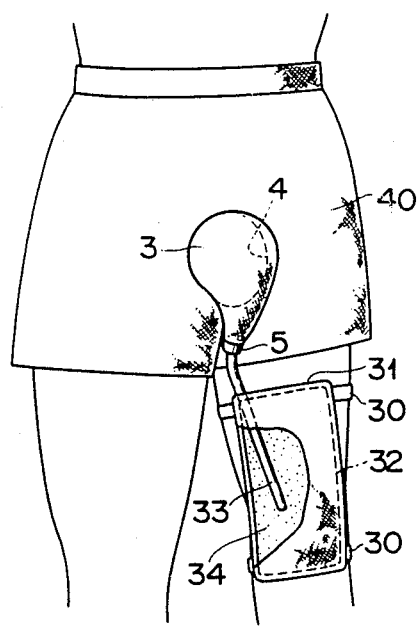

URINARY APPLIANCE

CROSS REFERENCES TO RELATED APPLICATIONS

This Application is a continuation of a patent application Ser. No. 835,240, filed Feb. 27, 1986, which is a continuation of the application Ser. No. 509,431, filed June 6, 1983, now abandoned.

TECHNICAL FIELD

This invention relates in general to a urinary appliance for use by the incontinent such as the aged, patients with spinal injuries and the like.

BACKGROUND ART

In general, urinary appliances have a urine receiving unit, which is applied to the patient's genitals, so as to receive the urine. A urinal or a urine receiving bag is connected to the urine receiving unit and stores the urine flowing from the urine receiving unit therein.

The conventional urine receiving unit is made of plastic or latex rubber and has the following problem. The inside of the urine receiving unit is cut off from the atmosphere and is kept sealed, moisture caused by the urine stays therein and the skin of the genitals can become irritated and sore because of this moisture. Moreover, the urine does not flow smoothly into the urinal or urine bag because the urine inside the urine receiving unit is not at atmospheric pressure. Furthermore, the plastic urine receiving unit is hard and inconvenient for the patient when walking.

It is an object of the present invention to provide a urinary appliance which prevents the moisture from remaining inside the genital receiving bag and thereby reduces skin irritation from becoming sore.

It is another object of the present invention to provide a urinary appliance which cause the urine to flow smoothly from the urine receiving bag to the urine bag or to the urinal.

It is still another object of the present invention to provide a urinary appliance which is suitable for the so-called "walking rehabilitation" of the patient.

DISCLOSURE OF THE INVENTION

The urinary appliance in accordance with the present invention is equipped with a urine or genital receiving bag made of a soft and flexible fabric which is permeable to air, and water repellent. Since the genital receiving bag is permeable to air, it is possible to prevent the skin of the genitals from becoming sore due to the moisture of the genital inside the urine receiving bag, and the flow of urine from the genital receiving bag to the urine storage bag or to the urinal becomes smooth. The genital does not leak from the urine receiving bag because the bag is water repellent. The genital receiving bag is soft and flexible and does not feel offensive to the patient or bearer of the bag so that he can walk easily.

In the urinary appliance in accordance with the present invention, a urine storage bag incorporating therein a highly water-absorbent resin is connected to the genital receiving bag. As urine flows from the genital receiving bag, the urine passes into the urine storage bag where the urine is absorbed by this water-absorbent resin, and changed into a gel and thus loses its fluidity. Hence, the patient or wearer of the urine storage bag can easily practice so-called "walking rehabilitation". The urine does not flow back from the urine storage bag to the genital receiving bag.

BRIEF DESCRIPTION OF DRAWINGS

FIG. 3 is a perspective view illustrating the genital receiving bag for a female incontinent patient in accordance with the present invention;

FIG. 4 is a partly enlarged sectional view of the genital receiving bag shown in FIG. 3;

FIGS. 5 through 7 are partly cut-away front views, each illustrating another embodiment of the present invention, being designed so as to enable the patient to walk easily;

BEST MODE FOR CARRYING OUT THE INVENTION

Figure 1:
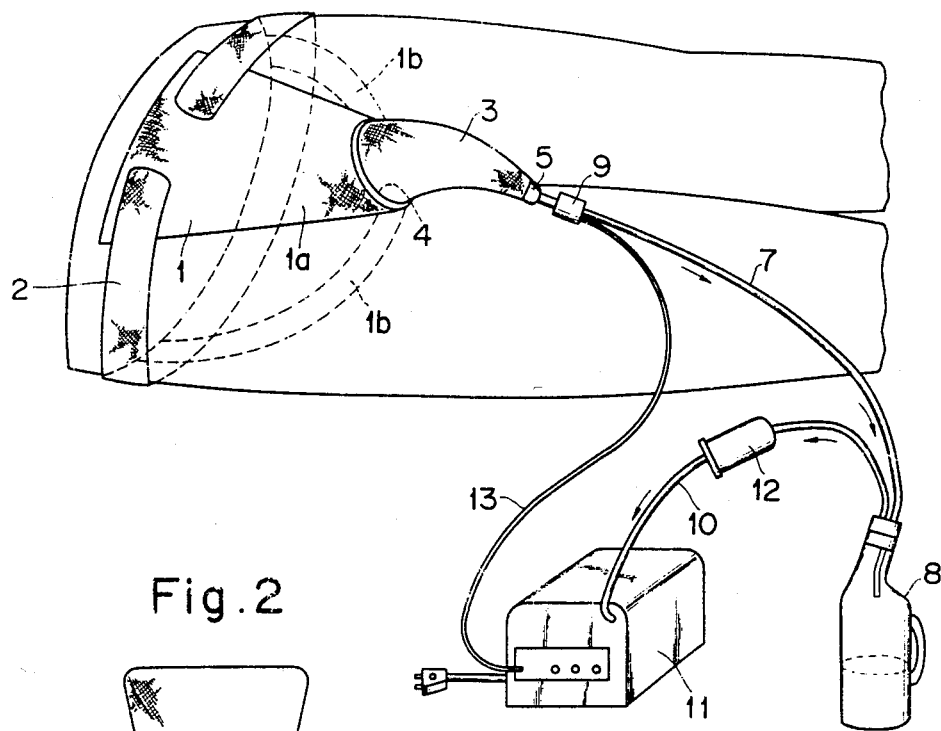
FIG. 1 shows one embodiment of the present invention and is a perspective view illustrating the urinary appliance for a male incontinent patient when lying down.
Figure 2:
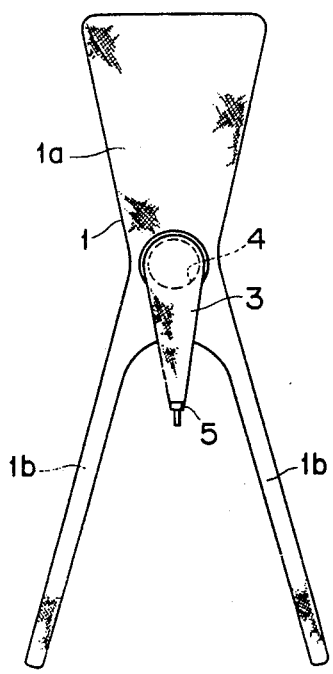
FIG. 2 is a front view of the device shown in FIG. 1.

One embodiment of the present invention will now be described with reference to FIGS. 1 and 2. The device 1 is shown fitted around the waist of a patient by a belt 2. The device 1 has a front section 1a which fits over the abdominal region of the patient, and two narrow elongated rear sections 1b, 1b which are positioned over the buttocks of the patient. These front and rear sections 1a, 1b, 1b are detachably fitted by the belt 2 by suitable means such as "magic tape" or Velcro. A urine or genital receiving bag 3 is fitted to the front section 1a of the device. 1. The genital receiving bag 3 in this embodiment has a shape suitable for the accommodation of the genitals of a man. The genital receiving bag 3 has an opening 4 at one of its ends and a urine outlet 5 at the other. The periphery of this opening 4 is fitted to the device 1. The genital receiving bag 3 is made of a soft and flexible fabric which is permeable to air, and water repellent. The fabric is a woven or non-woven fabric that has been treated with a water-repelling agent. If a woven fabric is used, it is possible to first treat the yarn prior to weaving, with the water-repelling agent and then weave the yarn to obtain the woven fabric. The fabric forming the urine receiving bag may be made of a porous resin membrane having through pores. The device 1 may also be formed of the same fabric as that of the genital receiving bag 3.

A urine storage unit 8 is connected to the urine outlet 5 of the genital receiving bag 3 via a tube 7. A sensor is fitted to the urine outlet 5, and a suction unit 11 is connected to the urine outlet 5 via another tube 10 with a deodorizing filter 12 interposed in the tube 10. The sensor 9 is electrically connected to the suction unit 11 via wires 13.

The operation of the urinary appliance having the construction described above will now be described. When the patient urinates when lying down, the urine is received by the genital receiving bag 3 and some of the urine reaches the sensor 9 through the urine outlet 5. The sensor 9 senses this urine and sends a detection signal to the suction unit 11. The suction unit 11 is actuated by this signal so that the air inside the urinal 8 is exhausted through an exhaust port (not shown) formed in the suction unit 11 through the tube 10. Since the inside of the urinal 8 is kept at a negative pressure in this case, the genital inside the urine receiving bag 3 is forced to flow into the urinal 8.

Since the genital receiving bag 3 is permeable to air, its interior is always at atmospheric pressure so that the genital inside the urine receiving bag 3 flows smoothly into the urinal 8 when the suction unit 11 is actuated as described above. Also, because the genital receiving bag 3 is permeable to air, the moisture generated by the urine does not stay inside the genital receiving bag 3 but evaporates through the surface of genital receiving bag 3. The air permeable fabric therefore, substantially prevents the moisture from remaining inside the genital receiving bag 3 and thereby helps reduce skin irritation and sores.

Since the genital receiving bag 3 is also water repellent, the urine neither leaks nor soaks in. Since the genital receiving bag is soft and flexible, it does not feel offensive to the patient.

FIGS. 3 and 4 illustrate the genital receiving bag 20 for a female incontinent patient. In the same way as the genital receiving bag 3 for the male patient shown in FIG. 1, this genital receiving bag 20 is made of a soft and flexible fabric that is permeable to air, and water repellent, and has an opening 21 and an urine outlet 22. The opening 21 has a relatively large area and a ring 23 is fitted around the opening. The ring 23 is made of a soft and flexible material having good shape retaining properties such as foam rubber, urethane foam, or the like. It is shaped in such a manner that it comes into contact with the periphery of the female genitals. The ring 23 has at one part of a flat tongue 23a and the rest of the ring is shaped to be round in cross-section. The tongue 23a is fitted to the perineum of the female genitals. The ring 23 is covered with a soft and flexible fabric 24 which is permeable to air and water repellent.

The genital receiving unit 3 for the male patient as well as the genital receiving unit 20 for the female patient may be detachably fitted to the device 1.

Figure 7:
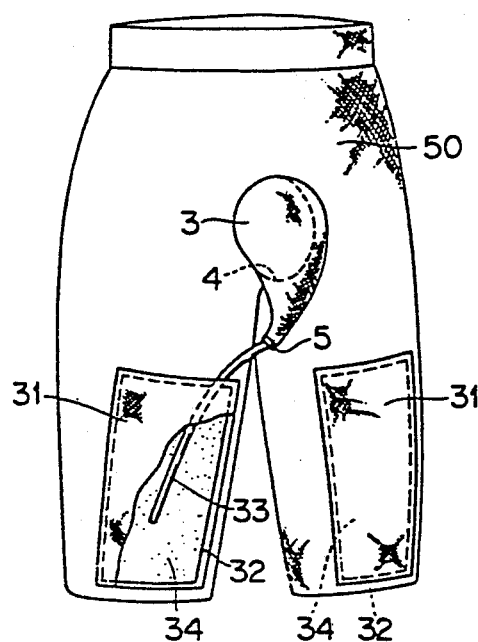

FIGS. 5 and 7 each show further embodiments of the present invention. These embodiments are specifically designed so that the incontinent patient can walk more easily.

In FIG. 5, an external bag 31 is shown fitted to one of the legs of the patient by a band 30. This external bag 31 is made of cloth, plastic or the like. A cloth bag is preferred in this embodiment because the bag comes into direct contact with the skin. The external bag 31 is open at its upper part so that it receives a urine storage bag 32. The urine storage bag 32 is made of rubber or plastic. A tube 33 connected to the urine outlet 5 of the genital receiving bag 3 is inserted into the urine storage bag 32 and is sealed in place. A highly water-absorbant resin 34 is placed inside the urine storage bag 32. The following can be listed as examples of the highly water-absorbant resin:

(1) starch-acrylonitrile grafted polymer types of highly water-absorbent resins;

(2) cellulose-acrylonitrile grafted polymer types of highly water-absorbent resins;

(3) carboxymethylated polysaccharide-acrylonitrile grafted polymer types of highly water-absorbent resins;

(4) polyacrylic acid types of highly water-absorbent resins;

(5) polyacrylonitrile types of highly water-absorbent resins;

(6) non-ionic polymer types of highly water-absorbent resins.

The highly water-absorbent resins may assume various forms such as fibers, cloth, cotton, powder, and so on. The water-absorbent resin 34 may be wrapped in craft paper or the like and is then placed in the urine storage bag 32.

The operation of the urinary appliance shown in FIG. 5 will now be described. When the patient urinates when standing, the urine is received by the genital receiving bag 3 and flows into the urine storage bag 32 via the tube 33 due to gravitational force. Since the genital receiving bag 3 is permeable to air, the genital inside the urine receiving bag 3 is at atmospheric pressure and flows smoothly into the urine storage bag 32. The urine is then absorbed by the highly water-absorbant resin 34 inside the urine storage bag 32, is changed into a gel and thus loses its fluidity. The patient can walk easily because the genital receiving bag 3 is soft and flexible and because the urine is the form of a gel inside the urine storage bag 32 and no longer flows.

Even if there are small holes in the urine storage bag 32, the gelled urine will neither leak nor flow back to the genital receiving bag 31. The highly water-absorbent resin can also absorb ammonia released by the decomposition of urine and can thus prevent the occurrence of offensive odors.

The gelled urine is removed from the urine storage bag 32 and is then discarded. The urine storage bag 32 itself may be disposed.

In FIG. 6, the genital receiving bag 3 is shown fitted to underpants 40 similar to ordinary underpants.

In FIG. 7, the genital receiving bag 3 is shown fitted to elongated underpants 50 and two external bags 31, 31 are also fitted to the underpants 50. Each external bag 31 has placed therein a urine storage bag 32 which in turn has placed therein the highly water-absorbant resin 34. One of the urine storage bags 32 is a spare.

Figure 8:
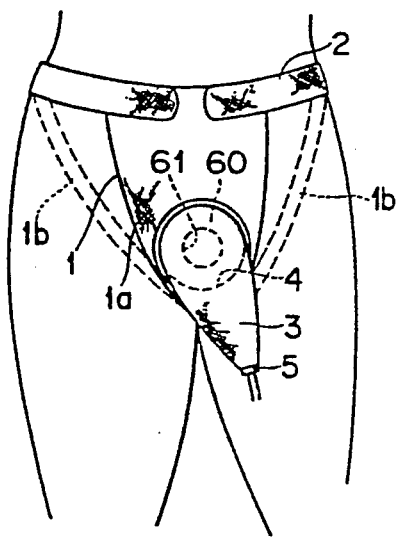
FIG. 8 is a front view illustrating an embodiment in which a modified genital receiving bag is fitted to the device.
Figure 9:
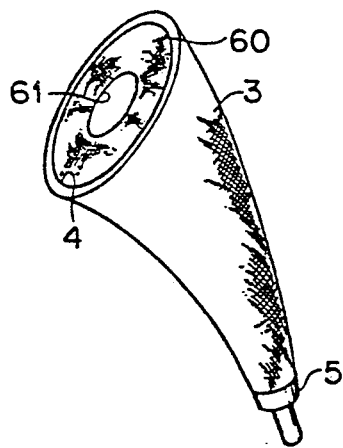
FIG. 9 is an enlarged perspective view of the genital receiving bag shown in FIG. 8.

FIGS. 8 and 9 show still another embodiment of the present invention. In this embodiment, a sealing sheet 60 is fitted around the periphery of the opening 4 of the genital receiving bag 3. The sealing sheet 60 is made of a soft and flexible fabric that is permeable to air, and water repellent. An insertion hole 61 is formed at the center of the sealing sheet 60 and the penis of the male patient is fitted into this insertion hole 61. When the patient urinates in any position such as lying, standing or sitting, using the urinary appliance of this embodiment, the urine passed into the genital receiving bag 3 does not flow back toward the abdominal region of the patient because it is cut off by the sealing sheet 60.

Figure 10:
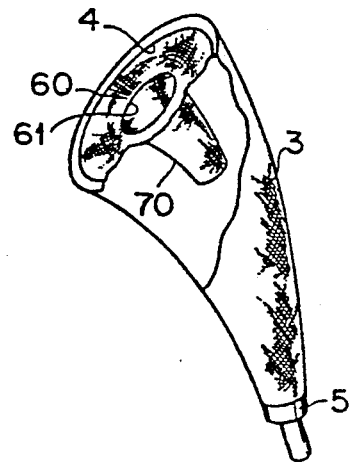
FIG. 10 is a partly cut-away perspective view illustrating another modified genital receiving bag.

FIG. 10 shows a further modified genital receiving bag 30. A cylinder 70 is further fitted around the periphery portion of the insertion hole 61. The cylinder 71 supports the penis of the male patient. The cylinder 70 is made of a soft and flexible fabric that is permeable to air, and water repellent, and is progressively tapered towards its tip. Since the size of the penis varies from patient to patient, the cylinder 70 is cut at a position suitable for that particular patient. Hence, the cylinder 70 can be smoothly and firmly fitted to the penis and can support the same.

What is claimed is:

1. A urinary appliance comprising a genital receiving bag, said genital receiving bag made of a soft and flexible material that is air permeable, and water repellent to permit air to escape therefrom to maintain the interior of said bag in continuous communication with atmospheric pressure;

an undergarment adapted to encircle a portion of a user's body, said undergarment having a pair of legs, each leg thereof being adapted with an external bag made of a soft, flexible fabric material;

said genital receiving bag is funnel shaped and including an opened substantially circularly shaped larger opening at one end thereof adapted to be fitted over a penis of a male user, and to engage the user's genital area adjacent the penis;

means for attaching removably said genital receiving bag to said undergarment;

said genital receiving bag further including an opened urine outlet at a smaller end thereof to allow the urine to escape therefrom;

said genital receiving bag being composed of cloth material, and enlarged at said larger end for increased capacity, to accommodate readily and comfortably variations in the size of the user's penis;

wherein said larger end of said genital receiving bag is closed partially by a sealing sheet;

said sealing sheet being generally annularly-shaped and composed of a flat, soft, flexible, fabric material that is permeable to air and water repellent;

said annular sealing sheet being attached to the genital receiving bag along the periphery of said larger end to extend tautly across the opening and to enable said sealing sheet to engage directly and conform to the shape of the genital area adjacent the penis of the user for sealing said sheet to the body of the user in a comfortable manner;

said annular sheet having an insertion hole to be fitted over the penis of the user, and a wide body-engageable portion extending from the periphery of said larger end of said genital receiving bag to said insertion hole, for sealing purposes;

a cylinder composed of a soft, flexible, cloth fabric material that is air permeable and water repellent and attached integrally to said sheet around a periphery of the insertion hole thereof for sealing said sheet to the penis of such a user;

said cylinder extending over a substantial portion of the axial length of the male penis to support the penis within said cylinder for enhancing the sealing engagement of the urinary appliance and for causing the penis to be spaced-apart from the inner surface of said genital receiving bag, for minimizing skin irritation resulting from the penis contacting and rubbing against the genital receiving bag;

a tube;

a first urine storage bag disposably contained in one of said external bags wherein said first urine storage bag is connected in fluid communication by said tube to the urine outlet of said genital receiving bag for receiving and storing urine;

wherein said first urine storage bag is substantially closed, and includes means defining a small opening through which said tube extends a substantial distance into said first urine storage bag, sufficient to prevent said tube from backing out of the interior of said first urine storage bag;

said tube having a relatively short length disposed outside of said first urine storage bag for reducing the risk of accidental disengagement from said first urine storage bag;

wherein a highly water-absorbent resin which absorbs the gels urine is disposed inside said first urine storage bag to absorb and gel urine and to inhibit the flow of urine back out of the urine storage bag;

a second urine storage bag disposably contained in the other of said external bags, said second urine storage bag being adapted to be connected in fluid communication by said tube to the urine outlet of said genital receiving bag for receiving and storing urine when said first urine storage bag becomes substantially full of gelled urine;

said second urine storage bag being substantially closed and including means defining a small opening through which said tube may be received and extended a substantial distance into said second urine storage bag, sufficient to prevent said tube from backing out of the interior of said second urine storage bag when received therein; and wherein a highly water-absorbent resin which absorbs and gels urine is disposed inside said second urine storage bag to absorb and gel urine and to inhibit the flow of urine back out of said second urine storage bag when said tube is inserted therein.

2. A urinary appliance according to claim 1, wherein said flexible material is made of woven fabric material.

3. A urinary appliance according to claim 1, wherein said flexible material is made of unwoven porous resin membrane.

* * * * *